United States Patent [19]

Dugast-Zrihen et al.

[11] Patent Number: 5,618,977

[45] Date of Patent: Apr. 8, 1997

[54] POLYIODINATED COMPOUNDS, PROCESS OF PREPARATION AND CONTRAST AGENT CONTAINING THEM

[75] Inventors: Maryse Dugast-Zrihen, Paris; Dominique Meyer, Saint-Maur, both of France

[73] Assignee: Guerbet S.A., Villepinte, France

[21] Appl. No.: 387,721

[22] PCT Filed: Aug. 24, 1993

[86] PCT No.: PCT/FR93/00824

§ 371 Date: Aug. 11, 1995

§ 102(e) Date: Aug. 11, 1995

[87] PCT Pub. No.: WO94/04488

PCT Pub. Date: Mar. 3, 1994

[30] Foreign Application Priority Data

Aug. 25, 1992 [FR] France ................................ 92 10270

[51] Int. Cl.⁶ ...................... C07C 237/46; C07C 237/42; C07C 235/16; A61K 49/04
[52] U.S. Cl. ...................... 564/153; 564/139; 424/9.451; 424/9.452
[58] Field of Search .................................. 424/9.43, 9.45, 424/9.452, 9.451; 564/135, 153

[56] References Cited

FOREIGN PATENT DOCUMENTS

| | | |
|---|---|---|
| 0308364 | 9/1988 | European Pat. Off. . |
| 0357467 | 6/1989 | European Pat. Off. . |
| 3429949 | 2/1986 | Germany . |

Primary Examiner—Gary E. Hollinden
Assistant Examiner—Michael G. Hartley
Attorney, Agent, or Firm—Jacobson, Price, Holman & Stern, PLLC

[57] ABSTRACT

The present invention relates to new polyiodinated compounds of general formula:

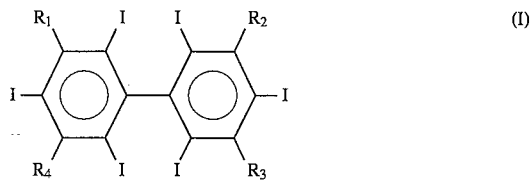

in which $R_1$ and $R_2$, which are identical to or different from each other, represent a group of formula:

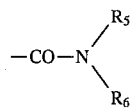

and $R_3$ and $R_4$, which are identical to or different from each other, represent a group of formula

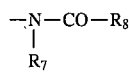

with $R_1$, $R_2$, $R_3$ and $R_4$ comprising in total at least ten hydroxyls, which can be used in contrast media for radiography.

The invention also relates to a process for the preparation of these compounds as well as to a contrast medium containing them.

9 Claims, No Drawings

POLYIODINATED COMPOUNDS, PROCESS OF PREPARATION AND CONTRAST AGENT CONTAINING THEM

The present invention relates to new polyiodinated compounds which can be used in contrast agents for radiography.

The invention also relates to a process for the preparation of these compounds and to the contrast agents containing them.

The subject matter of the invention is thus polyiodinated compounds of formula:

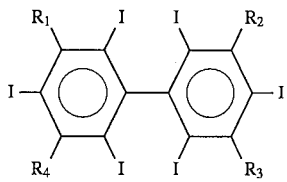   (I)

in which $R_1$ and $R_2$, which are identical to or different from each other, represent a group of formula:

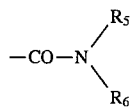

and $R_3$ and $R_4$, which are identical to or different from each other, represent a group of formula

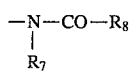

in which $R_5$ and $R_6$, and $R_7$ and $R_8$, which are identical to or different from each other, represent a hydrogen atom, a linear or branched $C_1$–$C_6$ alkyl, a linear or branched $C_1$–$C_6$ hydroxy- or polyhydroxyalkyl, optionally additionally containing one or more $C_1$–$C_6$ alkoxys, especially methoxy or ethoxy, a linear or branched $(C_1$–$C_6)$ alkoxy$(C_1$–$C_6)$alkyl or a linear or branched $(C_1$–$C_6)$ hydroxy- or polyhydroxyalkoxy $(C_1$–$C_6)$ alkyl, said substituents $R_1$, $R_2$, $R_3$ and $R_4$ comprising in total at least ten hydroxyls.

The preferred compounds are those of general formula (I) in which:

$R_5$, $R_6$ and $R_8$ are chosen from —$CH_3$, —$CH_2OH$, —$CH_2$—$CH_2OH$,

—CHOH—$CH_2OH$, 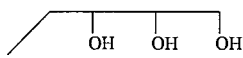

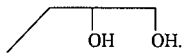, 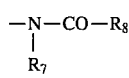

—$(CHOH)_4$—$CH_2OH$, —$CH_2OCH_3$ $R_7$ being as defined above.

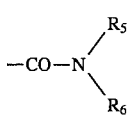

are those in which:

$R_5$ represents the

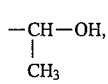

and $R_6$ is selected from —$CH_3$, —$CH_2$—$CH_2OH$ and

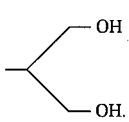.

Preferred groups $$-\underset{R_7}{\underset{|}{N}}-CO-R_8$$

are those in which:

$R_7$ is a defined above, $$-\underset{CH_3}{\underset{|}{CH}}-OH,$$

—CHOH—$CH_2OH$ and $R_8$ is selected from

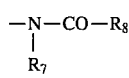

The preferred compounds of the present invention are those in which:

$R_1$ and $R_2$ represent

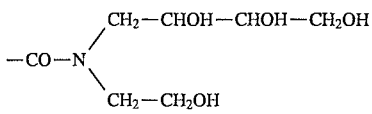

and $R_3$ and $R_4$ represent

—NH—CO—CHOH—$CH_2OH$     (compound No. 1);

$R_1$ and $R_2$ represent

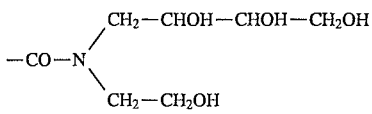

and $R_3$ and $R_4$ represent

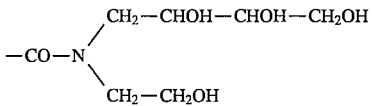     (compound No. 2)

$R_1$ and $R_2$ represent

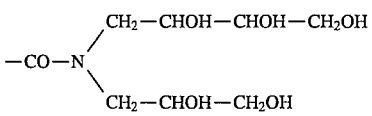

and $R_3$ and $R_4$ represent

—NH—CO—$CH_3$     (compound No. 3);

$R_1$ and $R_2$ represent

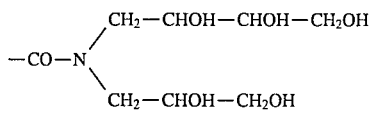

and $R_3$ and $R_4$ represent

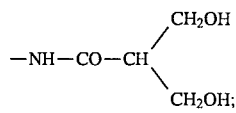 (compound No. 4)

$R_1$ and $R_2$ represent

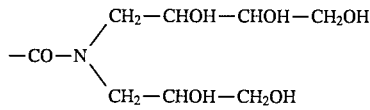

and $R_3$ and $R_4$ represent

—NH—CO—CHOH; (compound No. 5)
           |
          $CH_3$ $R_1$ and $R_2$ represent

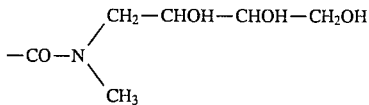

and $R_3$ and $R_4$ represent

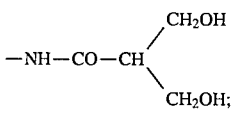 (compound No. 6)

$R_1$ and $R_2$ represent

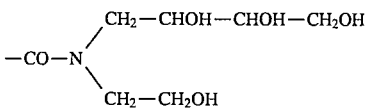

and $R_3$ and $R_4$ represent

—N—CO—$CH_3$ (compound No. 7)
 |
 $CH_2$
  \
   CHOH—$CH_2OH$;

$R_1$ and $R_2$ represent

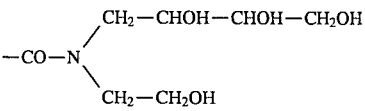

and $R_3$ and $R_4$ represent

—NH—CO—$CH_2OH$ (compound No. 8);

$R_1$ and $R_2$ represent

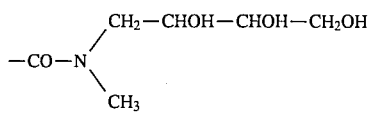

and $R_3$ and $R_4$ represent

—NH—CO—CHOH—$CH_2OH$ (compound No. 9);

$R_1$ and $R_2$ represent

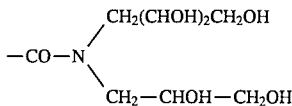

and $R_3$ and $R_4$ represent

—NH—CO—$CH_2OH$ (compound No. 10);

$R_1$ and $R_2$ represent

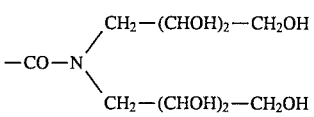

and $R_3$ and $R_4$ represent

—NH—CO—$CH_3$ (compound No. 11)

$R_1$ and $R_2$ represent

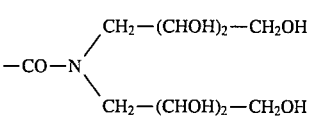

and $R_3$ and $R_4$ represent

—NH—CO—CHOH—$CH_3$ (compound No. 12).

The compounds of formula (I) of the present invention can be prepared by alkylation and/or acylation reactions.

The compounds of formula (I) of the present invention can especially be prepared by a process comprising the following stages:

a) coupling benzene derivatives of formulae (II) and (III):

 (II)

 (III)

X being selected from chlorine, bromine and iodine and $R'_1$ and $R'_2$ represent —$CO_2R$ with R representing $C_1$–$C_6$ alkyl, and $R'_3$ and $R'_4$ represent —$NO_2$, so as to produce a compound of formula (IV):

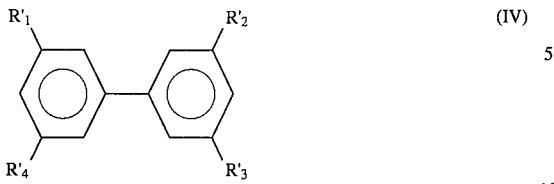

in which $R'_1$, $R'_2$, $R'_3$ and $R'_4$ are as defined above;

b) amidation of —$CO_2R$ with an amine

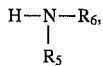

$R_5$ and $R_6$ being as defined above;

c) reduction of nitro groups to amino groups;
d) iodination under conventional conditions;
e) optional protection of hydroxyls using conventional protective groups;
f) acylation of aromatic amino groups with an acid chloride of formula $R'_8$—COCl, $R'_8$ representing a group $R_8$ as defined above in which hydroxyls are protected using a conventional protective group; and, either
g) optional alkylation of amido groups with a reagent of formula Z—$R_7$, Z being a labile group such as Cl, Br or I and $R_7$ being as defined above, and deprotection of protected hydroxyls; or
h) deprotection of protected hydroxyls and optionally alkylation of amido groups with a reagent of formula Z—$R_7$, Z being a labile group such as Cl, Br or I and $R_7$ being as defined above.

The reaction of stage a) preferably takes place in a suitable solvent such as xylene, nitrobenzene, nitrotoluene, DMF or pyridine, in the presence of a metal catalyst such as copper according to the Ullman method (E. Fanta, Chem. Rev., 64, 613, 1964).

The reaction of stage c) is a catalytic reduction by hydrogen on palladium charcoal or on Ranney nickel or a chemical reduction.

The iodination reaction of stage d) takes place under usual conditions, such as with aqueous ICl or $I_2$, in the presence of KI/ethylalnine at temperatures between 0° C. and 100° C.

The acylation and alkylation reactions of stages f) and g) are carried out under usual conditions, in the presence of a strong base.

The compounds of formula (I) of the present invention can also be prepared by a process comprising the following stages:

$a_1$) coupling of benzene derivatives of formulae (II) and (III) as described above, so as to obtain the compound of formula (IV) as described above;
$b_1$) saponification of ester groups —$CO_2R$ so as to obtain —$CO_2H$;
$c_1$) chlorination under usual conditions of acid groups so as to obtain —COCl;
$d_1$) amidation of —COCl with an amine of formula

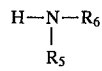

$R_5$ and $R_6$ being as defined above;

$e_1$) reduction of nitro to amino groups;

$f^1$) iodination under usual conditions;
$g^1$) optionally protection of —OH using conventional protective groups;
$h_1$) acylation of aromatic amino groups with an acid chloride of formula $R'_8$—COCl as described above in Stage f), and either;
$i_1$) optionally alkylation of amino groups with a reagent of formula Z—$R_7$ as described above in stage g), and deprotection of —OH, or
$j_1$) deprotection of —OH and optionally alkylation of amido groups with a reagent of formula Z—$R_7$ as described above in stage h).

The compounds of formula (I) of the present invention can also be prepared by a process comprising the following stages:

$a_2$) coupling of benzene derivatives of formulae (II) and (III)

X being selected from chlorine, bromine and iodine and $R'_1$ and $R'_2$ representing —$CO_2R$ with R representing H or $C_1$–$C_6$alkyl and $R'_3$ and $R'_4$ representing —$NO_2$, so as to obtain a compound of formula (IV):

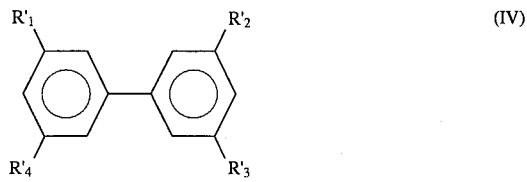

in which $R'_1$, $R'_2$, $R'_3$ and $R'_4$ are as defined above;
$b_2$) reduction of nitro to amino groups;
$c_2$) iodination under usual conditions, and either
$d_2$) chlorination of $^-CO_2R$ to COCl, followed by
$e_2$) acylation of aromatic amino groups with an acid chloride of formula $R'_8$COCl, $R'_8$ representing a $R_8$ group as defined above, or
$d'_2$) acylation of aromatic amino groups with an acid chloride of formula $R'_8$COCl, $R'_8$ representing a $R_8$ group as defined above, hydroxyls having been protected beforehand, followed by
$e'_2$) chlorination of —$CO_2R$ to —COCl, and
f2) amidation of —COCl with an amine of formula

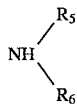

$R_5$ and $R_6$ being as defined above.

The amines of formula

used for the reactions of stages $f_2$) and $d_1$) mentioned above are, for the most part, known and commercially available. Additionally, amino alcohols used to produce the preferred compounds of the present invention, mentioned above, can be prepared in the following ways:

Preparation of the amino alcohol No. 1

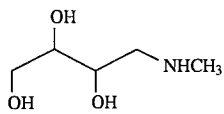

a) Preparation of the compound of formula

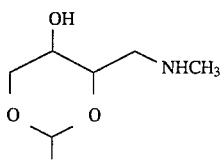

2 g (13.7 mmol) of 2,4-ethylidene-D-erythrose, obtained according to the process described in J. Am. Chem. Soc., 2301, 1960, Barker R. et al., are dissolved in 10 cm³ of water at 30° C. 10 cm³ of an aqueous methylamine solution (40%) are added dropwise at 0° C. After returning to room temperature, stirring is continued for 2 h. The solution is then reduced at room temperature in the presence of palladium-on-charcoal. The catalyst is then filtered and the filtrate concentrated to dryness. After solidification in ethyl ether, 1.7 g of the title product are obtained, i.e. a yield of 77%. TLC (dioxane/H₂O/NH₃:8/3/2) $R_f$: 0.74 TLC (CH₂Cl₂/MeOH 8/2) $R_f$: 0.17

$^{13}$C NMR (DMSO) (δ, ppm) 200 MHz 98.2 (C—CH₃), 80.3 (CH—O), 70.5 (CH₂—O), 63.4 (CHOH), 53.1 (CH₂—N), 36.5 (NH—CH₃), 20.7 (C—CH₃).

b) Preparation of the compound of formula:

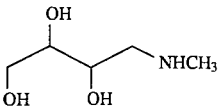

1.5 g (9.3 mmol) of the product obtained in a) are dissolved in 20 cm³ of 2N HCl. The solution is stirred at 50° C. for 5 h. After concentration, and purification by passing through H⁺ resin, the solution is evaporated to dryness. The residue is taken up in ethyl ether. After filtering and drying, 0.8 g of the title product is obtained (Yield: 64%). TLC (dioxane/H₂O/NH₃:8/3/2) $R_f$: 0.18

$^{13}$C NMR (DMSO) (δ, ppm) 200 MHz 74.5 (CH—CH₂OH), 69.6 (CHOHCH₂), 63.3 (CH₂OH), 54.7 (CH₂), 36.12 (NHCH₃) MS (DCI/NH₃) m/z; 153 (M+N⁺H₄); 136 (M+H⁺) base peak Preparation of amino alcohol No. 2

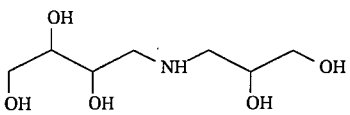

a) Preparation of the compound of formula:

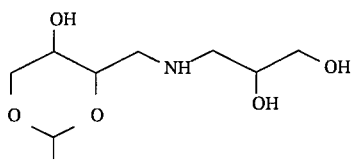

The compound is prepared according to the method described above.

Reductive amination of 2,4 -ethylidene-D-erythrose (6 g, 41 mmol) is carried out in the presence of aminopropanediol (1.2 equiv.) in ethanol (40 cm³).

After chromatography on a silica column, the title product is obtained with a yield of 73%. TLC (dioxane/H₂O/NH₃:8/3/2) $R_f$: 0.73

$^{13}$C NMR (DMSO) (δ, ppm) (200 MHz) (98, C—CH₃), (80.2–80.5, CH—O), (70.2–70.4, CH₂—O), (70.3, CHOH), (64.5–64.6, CH₂—OH), (62.2–63.1, CHOH), (52.9–53, CH₂), (50.8–51, CH₂), (20.5, CH₃).

b) Preparation of the compound of formula:

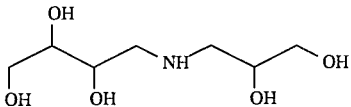

6 g (29.8 mmol) of the product obtained in the preceding stage are deprotected by treatment with 5N HCl (50 cm³). The reaction mixture is stirred for 4 h at 50° C. After evaporation, the residue obtained is purified through H⁺ resin. After concentration and solidification in ethyl ether, 2.6 g of the title product are obtained (Yield 54.7%) TLC (dioxane/H₂O/NH₃:8/3/2) $R_f$: 0.39

$^{13}$C NMR (DMSO) (δ, ppm) 74.3 (CH—CH₂OH, butanetriol chain), 70.3 (CH—CH₂)×2, 64.5–64.6 (CH₂OH, butanetriol chain), 63.3 (CH₂OH), 52.8 (CH₂N)×2 MS (DCI/NH₃) m/z 196 (M+H⁺) base peak, 178 (M+H⁺—H₂O), 160 (M+H⁺—2H₂O) 136, 122, 109, 92.

Preparation of amino alcohol No. 3

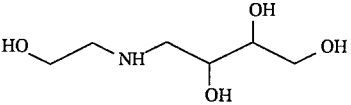

As with methylamine (for the preparation of amino alcohol No. 1) and aminopropanediol (for the preparation of amino alcohol No. 2), ethanolamine, under the same reductive amination conditions, leads, in the presence of 2,4-ethylidene-D-erythrose, to the title product.

a) Characteristics of the compound of formula

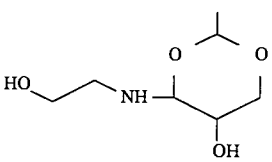

TLC (CH₂Cl₂/MeOH/NH₃: 8/2/1) $R_f$: 0.56

$^{13}$C NMR (DMSO) (δ, ppm) 97.9 (C—CH₃), 80.5 (CH—O), 70.2 (CH₂OH), 62.9 (CHOH), 60.2 (CH₂—O), 51.6 (CH₂—N), 50.7 (CH₂—N), 20.4 (CH₃).

b) Characteristics of the compound of formula

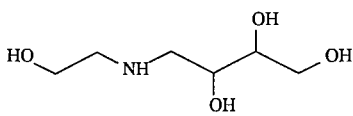

TLC ($CH_2Cl_2$/MeOH/$NH_2$ 55/30/10) $R_f$: 0.25 TLC (dioxane/$H_2O$/$NH_3$: 8/3/2) $R_f$: 0.48 $^{13}C$ NMR (DMSO) (δ, ppm) 74.5 ($\underline{C}$HOH$CH_2$OH), 70.2 ($\underline{C}$HOH—$CH_2$), 63.5 (CHOH $\underline{C}H_2$OH), 60.4 ($CH_2$—$\underline{C}H_2$OH), 52.5 ($\underline{C}H_2$—CHOH), 51.8 ($\underline{C}H_2CH_2$OH).

By taking the operating conditions described above and by using serinol with 2,4-ethylidene-D-erythrose, the amino alcohol of formula:

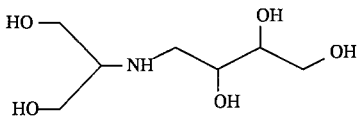

is prepared in the same way.
Preparation of the amino alcohol of formula:

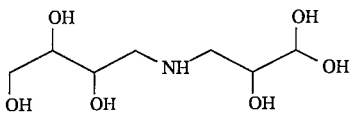

Butene-3,4-diol is prepared from butene-1,4-diol (commercially available from the company Aldrich-Strasbourg) according to the rearrangement method described in U.S. Pat. No. 4,661,646.

The epoxidation of butene-3,4-diol is carried out according to the method described in U.S. Pat. No. 3,352,898 and leads to 3,4-epoxy-1,2-butanediol.

The opening of the diol epoxide by benzylamine (0.5 eq.) leads to bis(2,3,4-trihydroxybutyl)benzylamine.

After debenzylation under hydrogen in the presence of palladium charcoal, bis(2,3,4trihydroxybutyl)amine is obtained.

It is obvious that the invention encompasses not only the compounds of formula (I) as a racemic mixture but also the stereoisomers such as enantiomers, diastereoisomers, atropoisomers, and syn-anti, endo-exo and E-Z isomers, due to the presence of asymmetric carbon atoms and/or to rotational restrictions due to steric hindrance introduced by the iodine atoms and/or by the substituents $R_1$ to $R_4$ of the compounds of formula (I).

Another subject matter of the present invention is contrast agents which comprise at least one compound of formula (I).

These contrast agents are useful in man and animals for radiological purposes.

The preferred pharmaceutical form of the contrast agents according to the invention consists of aqueous solutions of the compounds. According to one embodiment of the invention, the compounds are encapsulated inside liposomes.

The aqueous solutions generally contain a total of 5 to 100 g of compounds per 100 ml and the injectable amount of such solutions can generally vary from 1 to 1000 ml. The solutions can also contain additives such as a sodium salt, especially sodium citrate, heparin and edetate calcium disodium.

These compositions can be administered by any conventional route used for iodinated non-ionic contrast agents. Thus, they can be administered enterally or parenterally (intravenous routes, intra-arterial, opacification of the cavities) and in particular in the subarachnoid space.

Examples of the preparation of compounds according to the invention will be given below.

EXAMPLE 1

Preparation of 3,3'-bis[(2,3-dihydroxy)propionyl]amino-5,5'-bis[N-2-hydroxyethyl-N-2,3,4-trihydroxybutyl]carbamoyl-2,2',4,4',6,6'-hexaiodobiphenyl (compound No. 1).

1) Preparation of 3-iodo-5-nitrobenzoic acid 120 g (0.72 mol) of 3-nitrobenzoic acid are added to 122 g (0.53 mol) of $H_5IO_6$ and 400 g (1.57 mol) of iodine dissolved at 10° C. with stirring for 30 minutes in 2750 ml of 20% oleum. After stirring for 12 hours at room temperature, this solution is slowly poured into ice. The precipitate formed is filtered and then washed with a 20% sodium bisulphite solution before being dissolved in a sodium hydroxide solution and then filtered on paper. After acidification with HCl, there are obtained 170 g of white crystals which are filtered and dried.

Yield=81%

M.p.=172° C. TLC (toluene 60/methyl ethyl ketone 25/HCOOH 5) $R_f$=0.75 Iodine purity=99%

$^1H$ NMR (DMSO) 8.5 ppm (s, 2H aromatic protons) 8.7 ppm (s, 1H aromatic proton) 13 ppm (m, COO$\underline{H}$, 1H exchangeable with $D_2O$)

2) Preparation of the methyl ester of 3-iodo-5-nitrobenzoic acid 180 g (0.614 mol) of the compound obtained in 1), dissolved in 1800 ml of methanol and 10 ml of 98% $H_2SO_4$, are maintained under reflux for 24 hours. After evaporation of the methanol to two-thirds, the solution obtained is cooled and the ester which precipitates is filtered. After dissolving the product in 2000 ml of ether, the ethereal phase is washed with 1000 ml of $H_2O$, then dried over $MgSO_4$ and evaporated to dryness. 181 g of white crystals are obtained.

Yield=90%

M.p.=88° C. Iodine purity 99% TLC ($CH_2Cl_2$ 70/MeOH 30): $R_f$=0.95 IR 1720 ($COOCH_3$) 1520 ($NO_2$)

$^1H$ NMR (DMSO) 3.9 ppm (s, $COOCH_3$ 3H) 8.5 ppm (s, 2H aromatic protons) 8.7 ppm (s, 1H aromatic proton).

3) Preparation of 5,5'-dimethoxycarbony-3,3'-dinitrobiphenyl 86 g (0.28 mol) of the compound obtained in Stage 2) are brought to 220° C. After addition of 86 g of copper, the temperature is progressively increased to 270° C. and 20 g of copper are again added. The mixture is maintained at this temperature for 1 hour before being cooled. After extraction with $CH_2Cl_2$ and filtration through Celite, the organic phase is evaporated to dryness.

The residual paste is washed with 2×500 ml of petroleum ether and then taken up in ether. The brown precipitate formed is filtered off and then purified by silica chromatography. After evaporation, 20 g of brown crystals are obtained.

Yield=40%

M.p.=159° C. TLC ($CH_2Cl_2$): $R_f$=0.6

$^1H$ NMR (DMSO) 3.9 ppm (s, $COOC\underline{H}_3$ 6H) 8.5 ppm (2s, 4H aromatic protons) 8.7 ppm (1s, 2H aromatic protons)

4) Preparation of 5,5'-dicarboxy-3,3'-dinitrobipheny 14 g (0.038 mol) of the compound obtained in 3) are maintained under reflux for 18 h in 100 ml of a 25% aqueous NaOH solution.

The solution obtained is cooled; after acidification, the precipitate formed is extracted with ethyl acetate and washed with $H_2O$. After evaporation and washing with ether, 12 g of white crystals are obtained.

Yield=95%

M.p.>300° C. TLC (toluene 60/methyl ethyl ketone 25/HCOOH 25): $R_f=0.8$ $^1$H NMR (DMSO): 5.3 ppm (m, COOH, 2H exchangeable with D$_2$O) 8.65 to 8.8 ppm (3s, 6H aromatic protons).

5) Preparation of 3,3'-dinitro-5,5'-bis (N-hydroxyethyl-N-2,3,4-trihydroxybutyl)carbamoylbiphenyl 1.66 g (0.005 mol) of the compound obtained in 4) are added to a solution of 60 ml of SOCl$_2$ and 0.1 ml of dimethylformamide. The solution is maintained under reflux for 5 hours. After distillation of SOCl$_2$, the paste obtained is dissolved in CH$_2$Cl$_2$ and poured dropwise at 5° C. into a solution containing 3.3 g (0.02 mol) of N-2-hydroxyethyl-N-2,3,4-trihydroxybutylamine and 2.8 ml (0.02 mol) of triethylamine dissolved in 20 ml of dimethylacetamide. After addition, the mixture is stirred for 1 h at 60° C. and then at room temperature for 12 h. After filtration of the triethylamine hydrochloride, the solvent is evaporated. The paste obtained is purified by passing through H$^+$/OH$^-$ resin and then by chromatography on silica. After evaporation of the solvents and passing through H$^+$resin, 3.1 g of white crystals are obtained.

Yield=100% TLC (CH$_2$Cl$_2$ 60/meOH 40) $R_f$: 0.5.

6) Preparation of 3,3'-diamino-5,5'-bis[N-2-hydroxyethyl-N-(2,3,4-trihydroxybutyl)carbamoyl]-2,2',4,4',6,6'-hexaiodobiphenyl a) Reduction of the nitro groups:

1.3 g (0.002 tool) of the compound obtained in 5) dissolved in 60 ml of methanol in a 500 ml autoclave in the presence of 1 g of 10% aqueous Pd/C are stirred for 5H at 60° C. under a hydrogen pressure of 6×10$^5$ Pa. After filtration of the catalyst, the solution is used in the following stage. TLC (CH$_2$Cl$_2$ 40/MeOH 60): $R_f=0.15$.

b) Iodination with ICl 4.35 ml (0.024 mol) of a 70% ICl solution are added dropwise to the solution obtained in Stage a). On completion of addition, the reaction mixture is maintained at 80° C. for 18 h and then left for 12 h at room temperature. The brown solution obtained is evaporated, then iodination is repeated with 1.45 ml of 70% ICl in 20 ml of MeOH. After 10 h at 80° C., the solvent is evaporated and the paste washed with acetone. The product is taken up in ether and then dried. 2.1 g of white crystals are obtained.

Yield=80% TLC (CH$_2$Cl$_2$ 70/MeOH 30): $R_f=0.3$.

7) Preparation of 3,3'-diamino-5,5'-bis[N-acetoxyethyl-N-(2,3,4-triacetoxybutyl)cabomoyl]-2,2', 4,4',6,6'-hexaiodobiphenyl 64.6 ml of acetic anhydride are added dropwise at 5° C. to 42 g (0.0317 mol) of the compound obtained in 6) dissolved in 300 ml of pyridine. After stirring for 4 h at room temperature, the crude reaction product is poured into ice-cold water acidified with 750 ml of 5N HCl. The precipitate formed is filtered off and then taken up in CH$_2$Cl$_2$. The organic phase is washed with water and then dried over MgSO$_4$. After evaporation and purification on SiO$_2$/eluent ACOEt, there are obtained 20 g of white crystals which are washed with ether and dried.

Yield: 38% Iodine purity: 99% TLC (ACOEt) : $R_f=0.8$.

8) Preparation of 3,3'-bis[(2-isopropyl-1,3-dioxolan-5-yl)carbonylaminol]-5,5'-bis-[(N-acetoxyethyl-N-(2,3,4, -triacetoxybutyl)carbamoyl]-2,2',4,4',6,6'-hexaiodobiphenyl a) Preparation of the chloride of 4-(2-dimethyl-1-dioxolan-1-3-yl)carboxylic acid.

1.15 ml (0.02 mol) of oxalyl chloride are added to 2.2 g (0.012 mol) of the potassium salt of 4-(2-dimethyldioxolan-1-3-yl)carboxylic acid in 0.05 ml of pyridine and 12 ml of ether. After stirring for 2 h at 0° C. and then for 18 h at room temperature, the solution is evaporated to dryness.

b) The compound obtained in a) is slowly added to a solution of 2.7 g (0.002 mol) of the compound obtained in 7). After 16 h at 35°, the solution is poured onto Et$_2$O. After filtration, white crystals are obtained (3 g).

Yield: 93% TLC (ACOEt) : $R_f=0.75$.

9) Preparation of 3,3'-bis[[(2-3-dihydroxy)propionyl]-amino-5,5'-bis[N-2-hydroxyethyl-N-(2,3,4-trihydroxybutyl)]carbamoyl-2,2',4,4',6,6'-hexaiodobiphenyl 23 g (0.012 mol) of the compound obtained in 8) are stirred for 18 h at room temperature in the presence of 3.4 g of K$_2$CO$_3$ in 300 ml of MeOH. After evaporation, the residue is stirred in 150 ml of 2N HCl for 12 h at 25°. After removal of inorganics on H$^+$ resin, then OH$^-$ resin and then evaporation, 14 g (78%) of crude product are obtained. After purification on silica, 8 g (60%) of pure compound are obtained. TLC CH$_2$Cl$_2$ 50/MeOH 50: $R_f=0.1$% Iodine purity: 99%.

EXAMPLE 2

Preparation of 3,3'-bis(acetylamino)-5,5'-bis-[(N-2,3,4-trihydroxybutyl-N,2,3-dihydroxypropyl]carbamoyl-2,2',4,4',6,6'-hexaiodobiphenyl (compound No. 3)

1) Preparation of 5,5'-dicarboxy-3,3'-diaminobiphenyl 28.6 g (0.086 mol) of the compound obtained in 4) of Example 1 are suspended in 350 cm$^3$ of H$_2$O at pH 6.4. 3 g of Pd/C are added and the whole mixture is hydrogenated under a pressure of 5×10$^5$ pascals at 80° C. for 4 hours. The solution obtained after filtration of the Pd/C through Celite is brought back to pH 6 and the amino acid precipitates.

After filtration, 17 g of a cream-colored solid are obtained.

Yield: 78% TLC CH$_2$Cl$_2$/MeOH/NH$_3$:55/30/10 $R_f=0.8$.

2) Preparation of 5,5'-dicarboxy-3,3'-diamino-2,2',-4,4',6,6'-hexaiodobiphenyl 14.5 g (0.053 mol) of the compound obtained in 1) are suspended in 10 eq. of 70% ICl, 150 cm$^3$ of H$_2$O, 600 cm$^3$ of methanol and 2.5 cm$^3$ of concentrated HCl. The whole mixture is maintained at 80° C. for 72 hours. The reaction mixture is concentrated as much as possible. The brown oil obtained is stirred in 750 cm$^3$ of H$_2$O for 24 hours. The brown precipitate obtained is filtered. Crude weight: 46.5 g Yield: 68% TLC (ethanol): $R_f=0.7$.

3) Preparation of 3,3'-bis (diacetylamino)-5,5'-dicarboxy-2,2',4,4',6,6'-hexaiodobiphenyl 8.8 g (0.086 mol) of the compound obtained in 2) are dissolved in 150 cm$^3$ of DMAC and 6.1 cm$^3$ of acetyl chloride (10 eq) and are maintained at 45° C. with stirring for 56 hours.

The slightly concentrated reaction mixture is poured onto 200 cm$^3$ of ice-cold H$_2$O. After filtration of the precipitate, 10 g of a cream-colored solid are obtained.

Yield: 97% TLC (ethanol): $R_f=0.45$.

4) Preparation of 3,3'-bis (diacetylamino)-5,5'-di-(chloroformyl)-2,2',4,4',6,6'-hexaiodobiphenyl 9.3 g (0.0078 mol) of the compound obtained in 3) are dissolved in 100 cm$^3$ of thionyl chloride and maintained at reflux for 16 hours. After evaporation of the thionyl chloride, the product is crystallized by stirring in pentane. Weight obt.: 9.3 g Yield: 97% TLC (ethanol): $R_f=0.8$ 5) Preparation of 3,3'-bis (acetylamino)-5,5'-bis ([(N-2,3,4-trihydroxybutyl-N,2,3-dihydroxypropyl))carbamoyl-2,2',4,4',6,6'-hexaiodobiphenyl 8.7 g (0.0071 mol) of the compound obtained in 4) are dissolved in 100 cm$^3$ of DMAC.

4 cm$^3$ (4 eq.) of triethylamine are added, as well as 5.5 g (4 eq.) of N-2,3-dihydroxypropyl-N-2,3,4-trihydroxybutylamine.

The whole mixture is maintained at 70° C. for 4 hours (monitored by HPLC). After concentration of the reaction medium, the crude product is taken up in 100 cm³ of H₂O and brought to pH 10.5 by addition of 2N NaOH and maintained at 50° C. for 5 hours. After removal of inorganics with H⁺/OH⁻ resin, and then purification by silica chromatography, 3.5 g of the pure compound are obtained. TLC: $CH_2Cl_2$ 50/MeOH 50: $R_f$=0.1% Iodine purity: 98%.

EXAMPLE 3

Preparation of 3,3'-bis[(2-hydroxymethyl-3-hydroxy)propionyl]amino-5,5'-bis[N-(2-hydroxyethyl)-N-(2,3,4-trihydroxybutyl)carbamoyl-2,2',4,4',6,6'-hexaiodobiphenyl (compound No. 2)

1) Preparation of 3,3'-bis[(2-isopropyl-1,3-dioxan-5-yl)-carbonyl]amino-5,5'-bis[N-(2-acetoxyethyl)-N-(2,3,4-triacetoxybutyl)carbamoyl-2,2',4,4',6,6'-hexaiodobipenyl a) Preparation of the chloride of 2-isopropyl-1,3-dioxanyl-5-carboxylic acid 70 g (0.385 mol) of 2-isopropyl-1,3-dioxanyl-5-carboxylic acid are added portionwise to a solution of 400 ml of DMAC. The mixture is brought to 0° C. and then 31.2 ml (0.423 mol) of $SOCl_2$ are run in dropwise. On completion of addition, the mixture is left for 5 hours at room temperature.

b) 80 g (0.0482 mol) of the compound of Example 1 are added portionwise to the solution obtained in a). After 24 hours at 45° C., the solution is precipitated with water. After filtration, the precipitate obtained is taken up in $CH_2Cl_2$. The organic phase is washed with $H_2O$ and then dried over $MgSO_4$. After evaporation and purification on $SiO_2$ (eluent AcOEt), 70 g of beige crystals are obtained.

Yield=73% TLC (AcOEt): $R_f$=0.85.

2) Preparation of 3,3'-bis[(2-hydroxymethyl-3-hydroxy)-propionyl]amino-5,5'-bis[N-(2-hydroxyethyl)-N-(2,3,4-trihydroxybutyl)carbamoyl-2,2',4,4',6,6'-hexaiodobiphenyl 70 g (0.0355 mol) of the compound obtained in 1) are stirred for 18 hours at room temperature in the presence of 9 g of $K_2CO_3$ in 900 ml of MeOH. After evaporation the residue is stirred in 400 ml of HCl for 12 hours at 25° C.

After removing the inorganics with H⁺ resin, then OH⁻ resin and then evaporation, 41 g (76%) of white crystals are obtained. TLC ($CH_2Cl_2$ 50/MeOH 50): $R_f$=0.2 Iodine purity: 97.5%.

EXAMPLE 4

Preparation of 3,3'-bis[2-hydroxypropionylamino]-5,5'-bis[N-(2,3-dihydroxypropyl)-N-(2,3,4-trihydroxybutyl)carbamoyl]-2,2',4,4',6,6'-hexaiodobiphenyl (compound No. 5)

1) Preparation of 3,3'-dinitro-5,5-bis(N-2,3-dihydroxypropyl-N-2,3,4-trihydroxybutyl)carbamoylbiphenyl 12.5 g (0.0376 mol) of the compound obtained in 4) of Example 1 are added to a solution of 100 ml of $SOCl_2$ and 0.1 ml of DMF. The solution is maintained at reflux for 5 hours. After distillation of the $SOCl_2$, the paste obtained is dissolved in $CH_2Cl_2$ and poured dropwise at 20° C. into a solution containing 20.5 g (0.105 mol) of N-2,3-propanediol-N,2,3,4-trihydroxybutylamine and 14.6 ml (0.105 mol) of triethylamine dissolved in 80 ml of DMAC. After addition, the mixture is stirred for 4 hours at room temperature. After filtration of the triethylamine hydrochloride, the solvent is evaporated. The paste obtained is purified by passing on H⁺ resin. After evaporation of the solvent, 33 g of brown oil are obtained.

Yield=100% TLC ($CH_2Cl_2$/60: MeOH/40): $R_f$=0.15.
Preparation of 3,3'-diamino-5,5'-bis[N-2,3-dihydroxypropyl-N-(2,3,4-trihydroxybutyl)carbamoyl]-2,2', 4,4',6,6'-hexaiodobiphenyl a) Reduction of the nitro groups:

21 g (0.0306 mol) of the compound obtained in 1) dissolved in 800 ml of MeOH in a 1000 ml autoclave in the presence of 12 g of 10% aqueous Pd/C are stirred for 5 hours at 30° C. under a hydrogen pressure of 10⁶ Pa. After filtering the catalyst, the solution is used in the following stage. TLC ($CH_2Cl_2$/15: MeOH/85): $R_f$=0.15 b) Iodination with ICl:

54 ml (0.3 mol) of a 70% ICl solution are added dropwise to the solution obtained in Stage a). On completion of addition, the reaction mixture is left at room temperature for 12 hours. The solution is poured into 2000 ml of ether, the precipitate obtained is filtered and then washed with ether. After drying, the product obtained is iodinated again with 54 ml (0.3 mol) of 70% ICl in 500 ml of MeOH. After 12 hours at 50° C., the same treatment as above is applied to the solution. The precipitate obtained is iodinated again for a third time with 27 ml of ICl (0.15 mol) in 300 ml of MeOH.

After 12 hours at 50° C., the same treatment as above is applied to the solution. Cream-colored crystals are obtained. Weight=19 g - Yield=45% TLC ($CH_2Cl_2$/60: MeOH/40): $R_f$=0.25.

3) Preparation of 3,3'-diamino-5,5'-bis[(N-2,3-diacetoxypropyl-N-2,3,4-tracetoxybutyl)carbamoyl]-2,2', 4,4',6,6'-hexaiodobiphenyl 30 ml of acetic anhydride are added dropwise at 5° to 19 g (0.0137 mol) of the compound obtained in 2) dissolved in 110 ml of pyridine. After stirring for 12 hours at room temperature, the crude reaction product is poured into ice-cold water acidified with 150 ml of 5N HCl. The precipitate formed is filtered off and then taken up in $CH_2Cl_2$. The organic phase is washed with $H_2O$ and then dried over $MgSO_4$. After evaporation and purification on $SiO_2$, the eluent AcOEt, 11 g of yellow crystals are obtained.

Yield=46% Iodine purity=98.2% TLC (ACOEt) : $R_f$=0.8.

4) Preparation of 3,3'-bis[2-acetoxypropionylamino]-5,5'-bis[N-2,3 -diacetoxypropyl-N-(2,3,4-triacetoxybutyl)-carbamoyl]-2,2',4,4',6,6'-hexaiodobiphenyl a) Preparation of the chloride of 2-acetoxypropionic acid 40 ml of thionyl chloride are added dropwise to 50 g (0.378 mol) of 2-acetoxypropylcarboxylic acid dissolved in 60 ml of isopropyl ether. After reflux for 6 hours, the solution is evaporated and the residue is then distilled under reduced pressure. A white liquid is obtained.

Yield=60% Weight=30 g.

b) Acylation:

5.5 g (0.036 mol) of the compound obtained in a) are added slowly to a solution of 11 g (0.006 mol) of the compound obtained in 3) dissolved in 40 ml of DMAC.

After 16 hours at 40° C., the solution is poured into ice-cold water. The product is filtered, taken up in $CH_2Cl_2$, washed with $H_2O$ and then dried over $MgSO_4$. After evaporation and purification on $SiO_2$, eluent AcOEt, 3 g of yellow crystals are obtained.

Yield=35% TLC (AcOEt): $R_f$=0.7

5) Preparation of 3,3'-bis[2-hydroropionylamino]-5,5'-bis-[N-(2,3-dihydroxpropyl)-N-(2,3,4-trihydroxybutyl)carbamoyl]-2,2',4,4',6,6'-hexaiodophenyl 3 g (0.0015 mol) of the compound obtained in 4) are stirred for 12 hours at room temperature in the presence of 500 mg of $K_2CO_3$ in 60 ml of MeOH. After evaporation and removal of inorganics through H⁺ resin and then evaporation, 1 g of product is obtained.

Yield=70% TLC ($CH_2Cl_2$ 50/MeOH 50) $R_f$=0.3.

EXAMPLE 5

Preparation of 3,3'-bis[(2-hydroxymethyl-3-hydroxypropionyl)amino]-5,5'-bis[N-methyl-N-(2,3,4-trihydroxybutyl) - carbamoyl]-2,2',4,4',6,6'-hexaiodobiphenyl-(compound No. 6)

1) Preparation of 3,3'-dinitro-5,5'-bis(N-methyl-N-2,3,4-trihydroxybutyl)carbamoylbiphenyl 80 g (0.241 mol) of the compound obtained in 4° of Example 1 are added to a solution of 600 ml of $SOCl_2$ and 0.1 ml of DMF. The solution is maintained at reflux for 5 hours. After distillation of the $SOCl_2$, the paste obtained is dissolved in $CH_2Cl_2$ and poured dropwise at 20° C. into a solution containing 78 g (0.578 mol) of N-methyl-2,3,4-trihydroxybutylamine and 80 ml (0.578 mol) of triethylamine dissolved in 500 ml of DMAC. After addition, the mixture is stirred for 4 hours at room temperature. After filtration of the triethylamine hydrochloride, the solvent is evaporated. The paste obtained is purified by passing on $H^+$ resin. After evaporation of the solvent, 150 g of brown oil are obtained.

Yield=100% TLC ($CH_2Cl_2$)/75: MeOH/50): $R_f$=0.3

2) Preparation of 3,3'-diamino-5,5'-bis[N-methyl-N-(2,3,4-trihydroxybutyl)carbamoyl]-2,2',4,4',6,6'-hexaiodobiphenyl a) Reduction of the nitro groups.

20 g (0.0353 mol) of the compound obtained in 1) above in 700 ml of methanol in a 1000 ml autoclave in the presence of 10 g of 10% aqueous Pd/C are stirred for 5 hours at 30° C. under a hydrogen pressure of $10^6$ Pa. After filtering the catalyst, the solution is used in the following stage. TLC ($CH_2Cl_2$/40: MeOH/60): $R_f$=0.4.

b) Iodination with ICl 62 ml (0.353 mol) of a 10% ICl solution are added dropwise to the solution obtained in Stage a). On completion of addition, the reaction mixture is left at room temperature for 12 hours. The solution is poured into 2000 ml of ether, the precipitate obtained is filtered and then washed with ether. After drying, the product obtained is iodinated again with 31 ml of 70% ICl (0.17 mol) in 300 ml of MeOH. After 12 hours at 50° C., the same treatment as above is applied to the solution. Cream-colored crystals are obtained.

m=21 g

Yield=55% TLC ($CH_2Cl_2$/70: MeOH/30): $R_f$=0.4.

3) Preparation of 3,3'-diamino-5,5'-bis[N-methyl-N-(2,3,4-triacetoxybutyl)carbamoyl]-2,2',4,4',6,6'-hexaiodobihenyl 17.8 ml of acetic anhydride are added dropwise at 5° to 11.4 g (0.009 mol) of the compound obtained in 2) dissolved in 68 ml of pyridine. After stirring for 12 hours at room temperature, the crude reaction product is poured into ice-cold water acidified with 75 ml of 5N HCl. The precipitate formed is filtered off and then taken up in $CH_2Cl_2$. The organic phase is washed with $H_2O$ and then dried over $MgSO_4$. After evaporation and purification through $SiO_2$, eluent AcOEt, 9 g of white crystals are obtained.

Yield=66% Iodine purity=98% TLC (ACOEt) $R_f$=0.8

4) Preparation of 3,3'-bis[(2-isopropyl -1,3-dioxan-5-yl)carbonylamino]-5,5'-bis[N-methyl-N-(2,3,4-triacetoxybutyl)carbamoyl]-2,2',4,4',6,6'-hexaiodobiphenyl a) Preparation of the chloride of 2-isopropyl-1,3-dioxan-5-ylcarboxylic acid 1.8 g of 2-isopropyl-1,3-dioxan-5-ylcarboxylic acid ($10.5 \times 10^{-3}$ mol) are dissolved in 10 ml of DMAC. The mixture is brought to 0° C. and then 0.85 ml ($12 \times 10^{-3}$ mol) of $SOCl_2$ are added dropwise. After addition, the mixture is left for 5 hours at room temperature.

b) Acylation 2 g ($1.32 \times 10^{-3}$ mol) of the compound obtained in 3) are added to the solution obtained in a). After 12 hours at 45° C., the solution is poured into $H_2O$. After filtration, the product is taken up in $CH_2Cl_2$, washed with $H_2O$ and then dried over $MgSO_4$. After evaporation and purification through $SiO_2$, eluent AcOEt, 1 g of crystals is obtained.

Yield=50% Iodine purity=98.5% TLC (AcOEt) $R_f$=0.85

5) Preparation of 3,3'-bis[(2-hydroxymethyl)-3-hydroxypropionylamino]-5,5'-bis[(N-methyl-N-(2,3,4-trihydroxybutyl) carbamoyl]-2,2',4,4',6,6'-hexaiodobiphenyl 6 g (0.00328 mol) of the compound obtained in 4) are stirred for 12 hours at room temperature in the presence of 0.6 g of $K_2CO_3$ in 70 ml of methanol. After evaporation, the residue is stirred in 40 ml of 5N HCl for 12 hours at room temperature. After removal of the inorganics through $H^+$ resin and then $OH^-$ resin, and then evaporation, 3.75 g of white crystals are obtained.

Yield=78% Iodine purity: 98.7% TLC ($CH_2Cl_2$/50: MeOH/50) $R_f$=0.2

We claim:

1. Polyiodinated compounds of general formula:

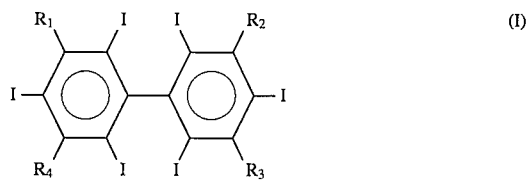

in which $R_1$ and $R_2$, which are identical to or different from each other, represent a group of formula:

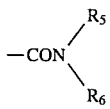

and $R_3$ and $R_4$, which are identical to or different from each other, represent a group of formula

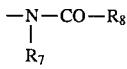

which $R_5$ and $R_6$, and $R_7$ and $R_8$, which are identical to or different from each other, represent a hydrogen atom, a linear or branched $C_1$–$C_6$ alkyl, a linear or branched $C_1$–$C_6$ hydroxy- or polyhydroxyalkyl, optionally additionally containing one or more $C_1$–$C_6$ alkoxys, a linear or branched ($C_1$–$C_6$) alkoxy($C_1$–$C_6$)alkyl or a linear or branched ($C_1$–$C_6$) hydroxy-or polyhydroxyalkoxy($C_1$–$C_6$)alkyl, said substituents $R_1$, $R_2$, $R_3$ and $R_4$ comprising in total at least ten hydroxyls.

2. Polyiodinated compounds of formula (I) according to claim 1, in which

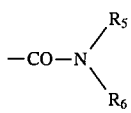

represents

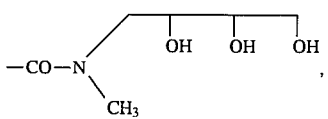

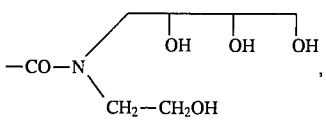

or

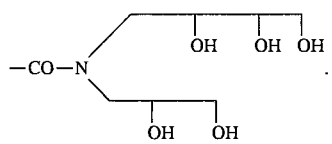

3. Polyiodinated compounds of formula (I) according to claim 1, in which

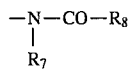

represents

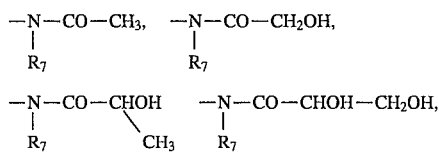

or

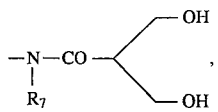

$R_7$ being as defined in claim 1.

4. Polyiodinated compounds of formula (I) according to claim 1, in which $R_1$ and $R_2$ are identical and represent

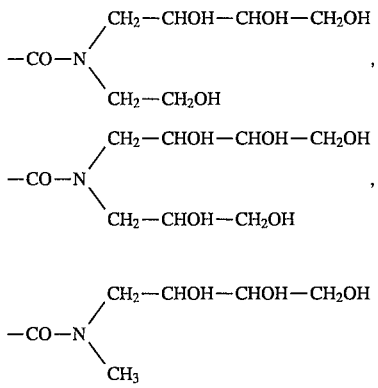

or $R_3$ and $R_4$ being identical and as defined in claim 1.

5. Polyiodinated compounds of formula (I) according to claim 1, in which $R_1$ and $R_2$ represent

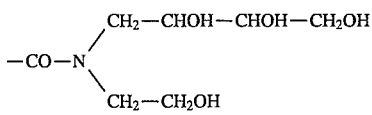

and $R_3$ and $R_4$ represent

$R_1$ and $R_2$ represent

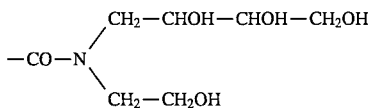

and $R_3$ and $R_4$ represent

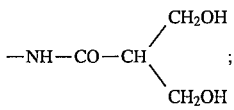

$R_1$ and $R_2$ represent

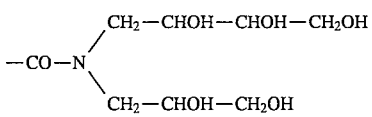

and $R_3$ and $R_4$ represent

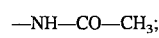

$R_1$ and $R_2$ represent

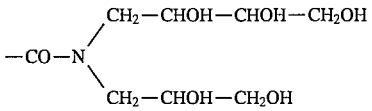

and $R_3$ and $R_4$ represent

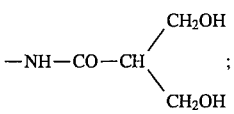

$R_1$ and $R_2$ represent

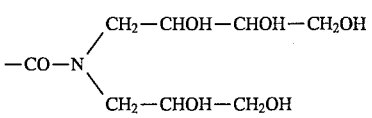

and $R_3$ and $R_4$ represent

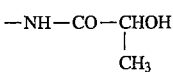

$R_1$ and $R_2$ represent

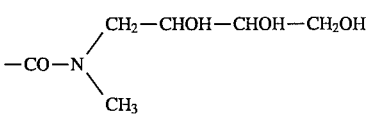

and $R_3$ and $R_4$ represent

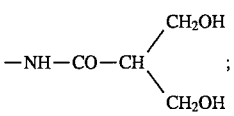

$R_1$ and $R_2$ represent

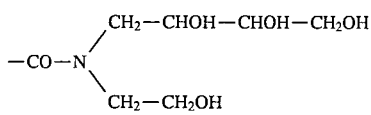

and $R_3$ and $R_4$ represent

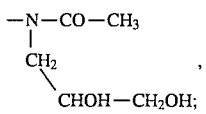

$R_1$ and $R_2$ represent

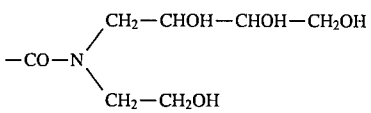

and $R_3$ and $R_4$ represent

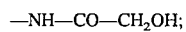

—NH—CO—CH$_2$OH;

$R_1$ and $R_2$ represent

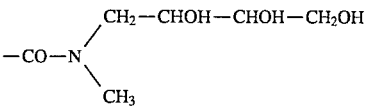

and $R_3$ and $R_4$ represent

—NH—CO—CHOH—CH$_2$OH $R_1$ and $R_2$ represent

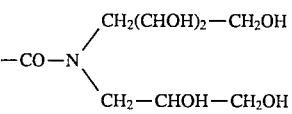

and $R_3$ and $R_4$ represent

—NH—CO—CH$_2$OH;

$R_1$ and $R_2$ represent

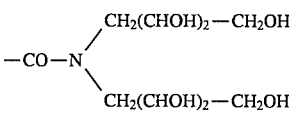

and $R_3$ and $R_4$ represent

—NH—CO—CH$_3$ $R_1$ and $R_2$ represent

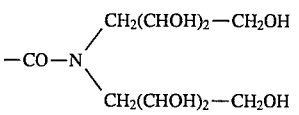

and $R_3$ and $R_4$ represent

—NH—CO—CHOH—CH$_3$.

6. Process for the preparation of the compounds of formula (I) according to claim 1, comprising the steps of:

a) coupling compounds of formulae:

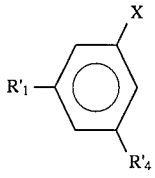

(II)

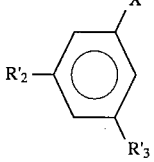

(III)

X being selected from chlorine, bromine and iodine and $R'_1$ and $R'_2$ representing —CO$_2$R, R being $C_1$-$C_6$ alkyl and $R'_3$ and $R'_4$ representing —NO$_2$, in a suitable solvent in the presence of a metal catalyst to produce a compound of formula (IV):

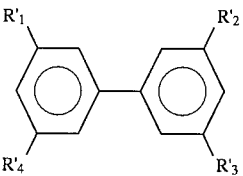

(IV)

b) amidation of —CO$_2$R with an amine of formula

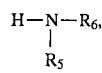

$R_5$ and $R_6$ being as defined in claim 1;

c) reduction of nitro groups to amino groups;

d) iodination under usual conditions;

e) optional protection of hydroxyls using conventional protective groups;

f) acylation of aromatic amino groups with an acid chloride of formula $R'_8$—COCl, $R'_8$ corresponding to $R_8$ as defined in claim 1 in which hydroxyls are protected; and, either g) optional alkylation of amido groups with a reagent of formula Z—$R_7$, Z being a labile group selected from Cl, Br and I and $R_7$ being as defined in claim 1, and deprotection of protected hydroxyls, or h) deprotection of protected hydroxyls and optionally alkylation of amido groups with a reagent of formula Z—$R_7$, Z being a labile group selected from Cl, Br and I and $R_7$ being as defined in claim 1.

7. Process for the preparation of the compounds of formula (I) according to claim 1, comprising the following steps:

a) coupling of benzene derivatives of formulae (II) and (III):

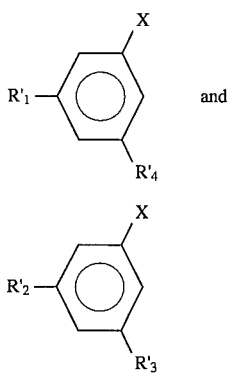

(II)

(III)

X being selected from chlorine, bromine and iodine and $R'_1$ and $R'_2$ representing $-CO_2R$ with R representing H or $C_1-C_6$ alkyl and $R'_3$ and $R'_4$ representing $-NO_2$, so as to obtain a compound of formula (IV):

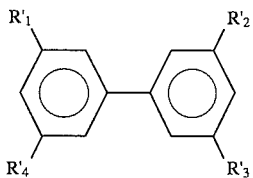

in which $R'_1$, $R'_2$, $R'_3$ and $R'_4$ are as defined above, b) reduction of nitro to amino groups,
c) iodination under usual conditions, and either
d) chlorination of $-CO_2R$ to COCl, followed by
e) acylation of aromatic amino groups with an acid chloride of formula $R'_8COCl$, $R'_8$ representing a $R_8$ group as defined in claim 1, or
d') acylation of aromatic amino groups with an acid chloride of formula $R'_8COCl$, $R'_8$ representing a $R_8$ group as defined in claim 1, hydroxyls having been protected beforehand, followed by
e') chlorination of $-CO_2R$ to COCl, and
f) amidation of COCl with an amine of formula

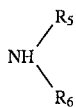

$R_5$ and $R_6$ being as defined in claim 1.

8. Contrast agent for radiology by X-rays, comprising at least one compound according to claim 1.

9. Contrast agent according to claim 8, consisting of an aqueous solution of the compound(s).

* * * * *